United States Patent [19]

Merkle et al.

[11] Patent Number: 5,840,913
[45] Date of Patent: Nov. 24, 1998

[54] PROCESS FOR PREPARING N-SUBSTITUTED PYRAZOLES

[75] Inventors: Hans Rupert Merkle, Ludwigshafen; Erich Fretschner, Neckarsteinach; Jürgen Schröder, Ludwigshafen, all of Germany

[73] Assignee: BASF Aktiengesellschaft, Ludwigshafen, Germany

[21] Appl. No.: 913,177

[22] PCT Filed: Feb. 27, 1996

[86] PCT No.: PCT/EP96/00790

§ 371 Date: Aug. 20, 1997

§ 102(e) Date: Aug. 20, 1997

[87] PCT Pub. No.: WO96/27589

PCT Pub. Date: Sep. 12, 1996

[30] Foreign Application Priority Data

| Mar. 4, 1995 | [DE] | Germany | 195 07 600.1 |
| Mar. 15, 1995 | [DE] | Germany | 195 09 361.5 |
| Mar. 18, 1995 | [DE] | Germany | 195 09 958.3 |

[51] Int. Cl.$^6$ ................................................. C07D 231/12
[52] U.S. Cl. ..................................... 548/373.1; 548/377.1
[58] Field of Search ............................... 548/377.1, 373.1

[56] References Cited

U.S. PATENT DOCUMENTS

| 3,907,824 | 9/1975 | Garber | 548/377.1 |
| 5,468,871 | 11/1995 | Ebel et al. | 548/373.1 |
| 5,705,656 | 1/1998 | Ono | 548/373.1 |

FOREIGN PATENT DOCUMENTS

| 0628563 | 12/1994 | European Pat. Off. | 548/377.1 |

Primary Examiner—Floyd D. Higel
Attorney, Agent, or Firm—John H. Shurtleff

[57] ABSTRACT

A process for the preparation of an N-alkyl- or N-phenylalkyl-substituted pyrazole I by reacting the corresponding N-unsubstituted pyrazole II with an alcohol III of the formula $R^1$—OH where $R^1$ is the same alkyl or phenylalkyl group to be added to the unsubstituted nitrogen group —NH— of the pyrazole reactant. Both of the reactants, i.e. the pyrazole II and alcohol III compounds, are catalytically reacted in the liquid phase in a molar ratio of from 0.001:1 to 1:1, at temperatures of 50°–400° C. and under a subatmosheric pressure of from 0.8 bar up to a superatmospheric pressure of 250 bar. The catalyst required for this liquid phase reaction is selected as being at least one or more non-heterogeneous acid catalysts, their alkyl esters or their acid anhydrides.

13 Claims, No Drawings

PROCESS FOR PREPARING N-SUBSTITUTED PYRAZOLES

This is a 371 of PCT/EP96/00790 filed Feb. 27, 1996.

The present invention relates to a process for the preparation of N-substituted pyrazoles by reacting pyrazoles with alcohols in liquid phase in the presence of catalysts at elevated temperatures.

DE-A-35 06 972 and U.S. Pat. No. 3,910,949 disclose a process for the N-alkylation of 3,5-diphenylpyrazoles, in which N-unsubstituted 3,5-diphenylpyrazoles are reacted with dimethyl sulfate/aqueous sodium hydroxide solution in the presence of a phase-transfer catalyst.

DE-A-24 25 979 describes the alkylation of 3,5-diarylpyrazoles with alkyl halides or dialkyl sulfates.

The disadvantages of these processes are the use of the very toxic and relatively costly dialkyl sulfates, because the major part of this molecule is not utilized, and the large amount of salt produced.

Chemical Letters (1992) 575–578 discloses a process for the N-alkylation of pyrazoles in which N-unsubstituted pyrazoles are reacted with alcohols in the presence of catalytic amounts of ruthenium, rhodium or iridium/trialkyl phosphite complexes.

The disadvantage of this process is the high cost of the catalysts.

DE-A 43 18 960 and DE-A-44 03 815 disclose a process for the N-alkylation of N-unsubstituted pyrazoles in which N-unsubstituted pyrazoles are reacted with alcohols or ethers in the presence of heterogeneous catalysts in the gas phase.

The disadvantage of this process is, especially in the case of very high-boiling N-unsubstituted pyrazoles, the need to vaporize the starting materials.

It is an object of the present invention to develop a more straightforward and less costly process for the preparation of N-substituted pyrazoles.

We have found that this object is achieved by a novel and improved process for the preparation of N-substituted pyrazoles of the general formula I

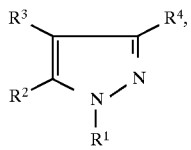

where
$R^1$ is $C_1$–$C_{12}$-alkyl or $C_7$–$C_{20}$-phenylalkyl and
$R^2$, $R^3$ and $R^4$ are, independently of one another, hydrogen, $C_1$–$C_{12}$-alkyl, $C_7$–$C_{20}$-phenylalkyl or unsubstituted or substituted aryl radicals,
by reacting pyrazoles of the general formula II

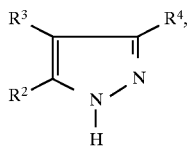

where $R^2$, $R^3$ and $R^4$ have the abovementioned meanings, with an alcohol of the general formula III

where $R^1$ has the abovementioned meanings, at from 50° to 400° C. in the presence of a catalyst, wherein the reaction of pyrazole II with compound III in the molar ratio of from 0.001:1 to 1:1 is carried out in liquid phase under a pressure which is slightly below atmospheric or up to a pressure of 250 bar, and acids and/or their alkyl esters or their anhydrides are used, in the molar ratio of from 0.0001:1 to 0.5:1 with respect to the pyrazole II, as catalyst.

The N-substituted pyrazoles I have a lower boiling point than the N-unsubstituted pyrazoles II and are continuously discharged in gaseous form with excess alkylating reagent III from the reactor, but discharge of the product during the reaction is not obligatory.

The process according to the invention can be carried out in the following way:

The reaction can be carried out by bringing a pyrazole II into contact with an alcohol III in the presence of a described catalyst at from 50° to 400° C., preferably 100° to 350° C. under a pressure which is slightly below or is above atmospheric, ie. a pressure of from 0.8 to 250 bar, preferably 0.8 to 100 bar, particularly preferably 0.9 to 100 bar.

The molar ratio of pyrazole II to compound III is, as a rule, from 0.001:1 to 1:1, preferably 0.002:1 to 1:1, particularly preferably 0.003:1 to 1:1.

The reaction is particularly preferably carried out at temperatures, under a pressure and with molar ratios at which the pyrazole II and the catalyst are in the liquid phase and the N-substituted pyrazole I and unreacted compound III are discharged in gaseous form together from the reaction vessel.

The pyrazole II and the catalyst can be initially dissolved or suspended in an inert solvent such as technical white oil or vacuum gas oil.

Suitable catalysts are compounds such as sulfuric acid, phosphoric acid, alkyl- or arylsulfonic acids and their alkyl esters or their anhydrides. The molar ratio of catalyst to pyrazole II is, as a rule, from 0.0001:1 to 0.5:1, preferably 0.0005:1 to 0.5:1, particularly preferably 0.01:1 to 0.2:1.

Compared with processes which have been disclosed, the process according to the invention provides N-substituted pyrazoles in a more straightforward and economic manner.

Suitable as starting compound II are pyrazoles such as pyrazole and substitued pyrazoles, 3-methylpyrazole, 4-methylpyrazole, 3,4-dimethylpyrazole, 3,5-dimethylpyrazole, 3,4,5-trimethylpyrazole, 3-ethylpyrazole, 4-ethylpyrazole, 3-arylpyrazoles, 3-phenylpyrazole, 3,5-diarylpyrazoles, 3,5-diphenylpyrazole, 3,4-diarylpyrazoles, 3,4-diphenylpyrazole, 3,4,5-triarylpyrazoles and 3,4,5-triphenylpyrazole.

Suitable as starting compound III are alcohols such as methanol, ethanol, n-propanol, isopropanol, n-butanol, tert-butanol and n-octanol, etc.

The N-substituted pyrazoles I which can be prepared by the process according to the invention are valuable starting materials for the preparation of dyes, drugs and crop protection agents.

The substituents $R^1$, $R^2$, $R^3$, $R^4$ and $R^5$ in the compounds I, II and III have the following meanings:

$R^1$, $R^2$, $R^3$ and $R^4$ independently of one another $C_1$–$C_{12}$-alkyl, preferably $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_4$-alkyl such as methyl, ethyl, n-propyl, isopropyl, n-butyl, isobutyl, sec-butyl and tert-butyl, $C_7$–$C_{20}$-phenylalkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^2$, $R^3$, $R^4$ independently of one another hydrogen aryl, preferably phenyl, substituted aryl radicals such as $C_7$–$C_{20}$-alkylphenyl, preferably $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl.

EXAMPLES

Example 1

50 g (0.2273 mol) of 3,5-diphenylpyrazole and 5 g (0.0437 mol) of 85% strength phosphoric acid were introduced into a bubble column at 250° C., a total of 158.2 g (4.94 mol) of methanol was passed through over the course of 4 hours, and the gaseous discharge was condensed. Subsequently two portions each of 50 g (0.2273 mol) of 3,5-diphenylpyrazole were introduced and reacted with 158.2 g (4.94 mol) of methanol in each case and condensed as before. Subsequently 31.5 g (0.143 mol) of 3,5-diphenylpyrazole were introduced, and 158.2 g (4.94 mol) of methanol were again passed through and condensed. Then 158.2 g (4.94 mol) of methanol were passed through without introducing 3,5-diphenylpyrazole. Each of these five batches was collected separately, analyzed by gas chromatography and concentrated under reduced pressure.

| Batch No.: | Molar ratio: 1-Methyl-3,5-diphenyl-pyrazole/3,5-diphenylpyrazole | Discharge [g] |
| --- | --- | --- |
| 1 | 94:6 | 29.4 |
| 2 | 96.9:3.1 | 46.4 |
| 3 | 97.8:2.2 | 47.1 |
| 4 | 94.7:5.3 | 35.3 |
| 5 | 100:0 | 23.7 |

A total of 181.5 g (0.825 mol) of 3,5-diphenylpyrazole and 791 g (24.7 mol) of methanol was used. A total of 175.8 g (91%) of 1-methyl- 3,5-diphenylpyrazole was obtained. The holdup of the bubble column was not taken into account.

Example 2

308.5 g (9.64 mol) of methanol were vaporized dropwise at 155° C. in an electrically heated column with a diameter of 4 cm and equipped with a sintered disk at the lower end and fitted onto a 250 ml two-neck flask over the course of 6 hours and passed through a melt, at 200° C., of 10 g (0.0455 mol) of 3,5-diphenylpyrazole and 0.046 g (0.000455 mol) of concentrated $H_2SO_4$. The gaseous discharge from the reaction was condensed and concentrated under reduced pressure. 10.2 g (92.5%) of 1-methyl-3,5-diphenylpyrazole were obtained, boiling point 190° C./3 mbar, with a content of 96.6% (GC).

Example 3

As in Example 2, a melt of 10 g (0.0455 mol) of 3,5-diphenylpyrazole and 0.051 g (0.000455 mol) of methyl sulfate was introduced and reacted over the course of 3 hours with 197.75 g (6.18 mol) of gaseous (vaporized at 160° C.) methanol. 9.7 g (86.7%) of 1-methyl-3,5-diphenylpyrazole were obtained, boiling point 190° C./3 mbar, with a content of 95.2% (GC).

Example 4

As in Example 2, a melt consisting of 10 g (0.0455 mol) of 3,5-diphenylpyrazole and 0.057 g (0.00455 mol) of dimethyl sulfate was prepared at 200° C. Over the course of 5 hours, 435 g (13.6 mol) of methanol were vaporized at 155° C. and passed through the melt which was maintained at 200° C. 10.4 g (96.9%) of 1-methyl-3,5-diphenylpyrazole were obtained, boiling point 190° C./3 mbar, with a content of 99.2% (GC).

Example 5

10 g (0.122 mol) of 4-methylpyrazole, 1.25 g (0.0122 mol) of sulfuric acid and 20 g of glass Raschig rings with a diameter of 3 mm were heated to 145° C. as in Example 2 and reacted at 145° C. over the course of 5 hours with 118.65 g (3.7 mol) of methanol vaporized at 170° C. After concentration under atmospheric pressure, 11.2 g (94.4%) of 1,4-dimethylpyrazole were obtained, boiling point 151° C., with a content of 98.6% (GC).

Example 6

As in Example 5, 10 g (0.122 mol) of 4-methylpyrazole were heated with 1.37 g (0.0122 mol) of methyl sulfate to 190° C. and reacted over the course of 3 hours with 79.1 g (2.47 mol) of methanol vaporized at 158° C. 11.5 g (93.5%) of 1,4-dimethylpyrazole were obtained, boiling point 151° C., with a content of 95.2% (GC).

Example 7

As in Example 5, 10 g (0.122 mol) of 4-methylpyrazole were heated with 1.54 g (0.0122 mol) of dimethyl sulfate to 195° C. and reacted over the course of 3 hours with 118.72 g (3.71 mol) of methanol vaporized at 155° C. 11.6 g (95.4%) of 1,4-dimethylpyrazole were obtained, boiling point 151° C., with a content of 96.3% (GC).

Example 8

As in Example 5, 10 g (0.122 mol) of 4-methylpyrazole were heated with 2 g (0.025 mol) of sulfur trioxide to 160° C. and reacted over the course of 4 hours with 180 g (5.63 mol) of methanol vaporized at 130° C. 10.6 g (84.9%) of 1,4-dimethylpyrazole were obtained, boiling point 151° C., with a content of 93.8% (GC).

Example 9

As in Example 5, 10 g (0.122 mol) of 4-methylpyrazole were heated with 2 g (0.014 mol) of phosphorus pentoxide to 150° C. and reacted over the course of 3.5 hours with 175 g (5.5 mol) of methanol vaporized at 125° C. 10.9 g (89.5%) of 1,4-dimethylpyrazole were obtained, boiling point 151° C., with a content of 96.2% (GC).

Example 10

As in Example 2, a melt of 10 g (0.0455 mol) of 3,5-diphenylpyrazole and 0.72 g (0.00455 mol) of benzenesulfonic acid was introduced and reacted over the course of 4.5 hours with 245 g (7.66 mol) of gaseous methanol (vaporized at 160° C.). 9.6 g (88.5%) of 1-methyl-3,5-diphenylpyrazole were obtained, boiling point 190° C./3 mbar, with a content of 98.2% (GC).

Example 11

As in Example 2, a melt of 10 g (0.0455 mol) of 3,5-diphenylpyrazole and 0.44 g (0.0045 mol) of methanesulfonic acid was introduced and reacted over the course of 4 hours with 175 g (5.46 mol) of gaseous methanol (vaporized at 160° C.). 10 g (92%) of 1-methyl-3,5-diphenylpyrazole were obtained, boiling point 190° C./3 mbar, with a content of 98% (GC).

Example 12

As in Example 2, the column was charged with 30 g of glass rings of diameter 3 mm, 16.4 g (0.24 mol) of pyrazole and 1.02 g (0.01 mol) of 96% by weight sulfuric acid, heated to 195° C. and reacted over the course of 7 hours with 703 g (9.5 mol) of tert-butanol vaporized at 180° C. 21.7 g of N-tert-butylpyrazole were obtained, boiling point 103° C., with a content of 99.4% (GC), which corresponds to a yield of 72.5%.

Example 13

20.5 g (0.25 mol) of 4-methylpyrazole, 82 g (0.65 mol) of n-octanol and 1.28 g (0.0125 mol) of 96% by weight sulfuric acid were stirred at 175° C. for 33 hours. After cooling, the mixture was extracted three times with 15 ml of 5% strength sulfuric acid each time.

The combined sulfuric acid extracts were neutralized with 25% strength sodium hydroxide solution. Subsequent distillation afforded 13.5 g of product which was, according to GC analysis, 99.3% unreacted 4-methylpyrazole.

17.4 g of 4-methyl-N-octylpyrazole were obtained from the organic phase, boiling point 75° C./7 mbar, with a content of 95% (GC) and with a conversion of 34.6% and a selectivity of 98.5%.

Example 14

6.8 g (0.1 mol) of pyrazole, 23.7 g (0.32 mol) of tert-butanol and 0.51 g (0.005 mol) of 96% by weight sulfuric acid were stirred in an autoclave at 200° C. and 35 bar for 3 hours. After cooling, decompression (expulsion of isobutylene) and phase separation, 6.5 g of an aqueous pyrazole solution, which was 10.2% by weight according to GC analysis, were obtained, and distillation thereof yielded 0.66 g of pyrazole. 10.5 g (83.6%) of N-tert-butylpyrazole were obtained from the organic phase, boiling point 102° C., with a content of 98.8% (GC).

Example 15

34 g (0.5 mol) of pyrazole and 83 g (0.64 mol) of 2-ethyl-1-hexanol were stirred with 2.55 g (0.025 mol) of 96% by weight sulfuric acid at 175° C. for 20 hours. After cooling, the mixture was extracted three times with 15 ml of 5% strength sulfuric acid each time. The combined sulfuric acid extracts were neutralized with 25% strength sodium hydroxide solution. Subsequent distillation afforded 27.0 g of, according to GC analysis, 99.1% pure unreacted pyrazole. 19.6 g of N-2-ethylhexylpyrazole were obtained from the organic phase, boiling point 65° C./50 mbar, with a content of 92% (GC) and with a conversion of 21.3% and a selectivity of 93.9%.

We claim:

1. A process for the preparation of N-substituted pyrazoles of the formula I

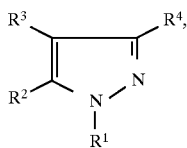

where $R^1$ is $C_1$–$C_{12}$-alkyl or $C_7$–$C_{20}$-phenylalkyl and $R^2$, $R^3$ and $R^4$ are, independently of one another, hydrogen, $C_1$–$C_{12}$-alkyl, $C_7$–$C_{20}$-phenylalkyl or unsubstituted or substituted aryl radicals, which comprises catalytically reacting pyrazoles of the formula II

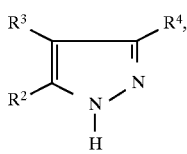

where $R^2$, $R^3$ and $R^4$ have the abovementioned meanings, with an alcohol of the formula III

where $R^1$ has the abovementioned meanings, at from 50° to 400° C. in the molar ratio of from 0.001:1 to 1:1 in liquid phase under a subatmospheric pressure of 0.8 bar up to a superatmospheric pressure of 250 bar, selecting only acids or their alkyl esters or their anhydrides, in the molar ratio of from 0.0001:1 to 0.5:1 with respect to the pyrazole II, as catalyst.

2. A process as claimed in claim 1, selecting at least one of sulfuric acid, alkyl sulfates, dialkyl sulfates, phosphoric acid, alkyl phosphates, alkylsulfonic acids or their alkyl esters, arylsulfonic acids or their alkyl esters, and the anhydrides of said acids as catalyst.

3. A process as claimed in claim 1, wherein the molar ratio of pyrazole II to compound III is from 0.002:1 to 1:1.

4. A process as claimed in claim 1, wherein the molar ratio of pyrazole II to compound III is from 0.003:1 to 1:1.

5. A process as claimed in claim 1, wherein the molar ratio of catalyst to the pyrazole II is from 0.0005:1 to 0.5:1.

6. A process as claimed in claim 1, wherein the molar ratio of catalyst to the pyrazole II is from 0.01:1 to 0.2:1.

7. A process as claimed in claim 1, wherein the reaction is carried out under a pressure of from 0.8 to 100 bar.

8. A process as claimed in claim 1, wherein the reaction is carried out under a pressure of from 0.9 to 100 bar.

9. A process as claimed in claim 1, wherein the reaction is carried out at from 100° to 350° C.

10. A process as claimed in claim 1, selecting at least one of sulfur trioxide or phosphorus pentoxide as said catalyst.

11. A process as claimed in claim 1, wherein the pyrazole II is selected from the group consisting of pyrazole, 3-methylpyrazole, 4-methylpyrazole, 3,4-dimethylpyrazole, 3,5-dimethylpyrazole, 3,4,5-trimethylpyrazole, 3-ethylpyrazole, 4-ethylpyrazole, 3-phenylpyrazole, 4-phenylpyrazole, 3,4-diphenylpyrazole, 3,5-diphenylpyrazole and 3,4,5-triphenylpyrazole.

12. A process as claimed in claim 1, wherein the pyrazole II is selected from the group consisting of pyrazole, 4-methylpyrazole and 3,5-diphenylpyrazole.

13. A process as claimed in claim 1, wherein the alcohol III is selected from the group consisting of methanol, ethanol, n-propanol, isopropanol, n-butanol, tert-butanol and n-octanol.

* * * * *